United States Patent
Koga et al.

(10) Patent No.: US 10,132,795 B2
(45) Date of Patent: Nov. 20, 2018

(54) METHOD FOR EVALUATING OR SELECTING AGENT FOR SUPPRESSING GIP LEVEL ELEVATION

(71) Applicant: Kao Corporation, Chuo-ku, Tokyo (JP)

(72) Inventors: Yoshitaka Koga, Utsunomiya (JP); Noriko Osaki, Utsunomiya (JP); Manabu Watanabe, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/128,666

(22) PCT Filed: Mar. 6, 2015

(86) PCT No.: PCT/JP2015/056603
§ 371 (c)(1),
(2) Date: Sep. 23, 2016

(87) PCT Pub. No.: WO2015/146537
PCT Pub. Date: Oct. 1, 2015

(65) Prior Publication Data
US 2017/0227526 A1    Aug. 10, 2017

(30) Foreign Application Priority Data

Mar. 24, 2014  (JP) ................. 2014-060341
Mar. 2, 2015   (JP) ................. 2015-040187

(51) Int. Cl.
*G01N 33/50*    (2006.01)
*C12Q 1/68*     (2018.01)
*G01N 33/92*    (2006.01)

(52) U.S. Cl.
CPC .......... *G01N 33/5023* (2013.01); *C12Q 1/68* (2013.01); *G01N 33/92* (2013.01); *G01N 2500/10* (2013.01); *G01N 2800/042* (2013.01)

(58) Field of Classification Search
CPC ............................................... G01N 33/5023
See application file for complete search history.

(56) References Cited

U.S. PATENT DOCUMENTS

| | | | |
|---|---|---|---|
| 2002/0035064 | A1 | 3/2002 | Robl et al. |
| 2003/0166724 | A1 | 9/2003 | Hangeland |
| 2004/0229807 | A1 | 11/2004 | Robl et al. |
| 2009/0076033 | A1 | 3/2009 | Robl et al. |
| 2012/0122772 | A1 | 5/2012 | Ishimaru et al. |
| 2013/0281367 | A1 | 10/2013 | Ishirnaru et al. |

FOREIGN PATENT DOCUMENTS

| | | | |
|---|---|---|---|
| CN | 1319012 | A | 10/2001 |
| CN | 102470145 | A | 5/2012 |
| CN | 102961388 | A | 3/2013 |
| CN | 103298478 | A | 9/2013 |
| JP | 2002-524517 | A | 8/2002 |
| JP | 2004-065194 | A | 3/2004 |
| JP | 2011-080803 | A | 4/2011 |
| JP | 2011-080804 | A | 4/2011 |
| JP | 2012-171914 | A | 9/2012 |
| JP | 2012-171915 | A | 9/2012 |
| WO | WO 98/24464 | A1 | 6/1998 |
| WO | WO 00/15229 | A1 | 3/2000 |
| WO | WO 2010/102171 | A2 | 9/2010 |

OTHER PUBLICATIONS

Sommer, C.A. et al., "RNA-Seq analysis of enteroendocrine cells reveals a role for FABP5 in the control of GIP secretion," Mol Endocrinol. Nov. 2014; 28(11):1855-65. doi: 10.1210/me.2014-1194. Epub Sep. 30, 2014; Endocrine Society, Baltimore, MD.

Yamada, Y., "New diabetes mellitus treatment—Various action of incretin considering the possibility of the incretin therapy out of the pancreas; Extra-pancreatic effects of GIP and GLP-1," Journal of Clinical and Experimental Med. 2009; 231(7):759-762.

Extended European search report including the supplementary European search report and the European search opinion, for EP Appl. No. 15769760.8, dated Aug. 28, 2017, European Patent Office, Munich, Germany.

Haider, DG et al., "Plasma adipocyte and epidermal fatty acid binding protein is reduced after weight loss in obesity," Diabetes Obes Metab. Sep. 2007;9(5):761-3. Epub Mar. 13, 2007, Wiley-Blackwell, Oxford, England.

Marks, V, "Human obesity: its hormonal basis and the role of gastric inhibitory polypeptide," Med Princ Pract. 2006;15(5):325-37, Karger, Basel, Switzerland.

Shibue, K et al., "Fatty acid-binding protein 5 regulates diet-induced obesity via GIP secretion from enteroendocrine K cells in response to fat ingestion," Am J Physiol Endocrinol Metab. Apr. 1, 2015;308(7):E583-91. doi: 10.1152/ajpendo.00543.2014. Epub Jan. 27, 2015, American Physiological Society, Bethesda, MD.

Shibue, K et al., "FABP5 is an essential modulator of fatty acid-induced GIP secretion in enteroendocrine K cells," Diabetologia. Sep. 2014;57 Suppl 1, pp. S309-S310, Abstract No. 766, Abstracts of the 50th EASD Annual Meeting, Sep. 15-19, 2014, Vienna, Austria, doi: 10.1007/s00125-014-3355-0, Springer Verlag, Berlin, Germany.

(Continued)

*Primary Examiner* — Gyan Chandra
(74) *Attorney, Agent, or Firm* — Sterne, Kessler, Goldstein & Fox P.L.L.C.

(57) ABSTRACT

A method for evaluating or selecting an agent for suppressing GIP level elevation, comprising the following steps (A) to (D): (A) contacting a test substance with a mammal-derived tissue or cell capable of expressing an FABP4 gene or FABP5 gene, or an FABP4 protein or FABP5 protein; (B) measuring an expression level of the FABP4 gene or FABP5 gene, an expression level of the FABP4 protein or FABP5 protein, or an activity of the FABP4 protein or FABP5 protein in the mammal-derived tissue or cell; (C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and (D) evaluating or selecting a test substance which reduces the expression level of the FABP4 gene or FABP5 gene, the expression level of the FABP4 protein or FABP5 protein, or the activity of the FABP4 protein or FABP5 protein as an agent suppressing GIP level elevation based on results of the above (C).

11 Claims, 6 Drawing Sheets

(56) References Cited

OTHER PUBLICATIONS

Wook, K et al., "The role of incretins in glucose homeostasis and diabetes treatment," Pharmacol Rev. Dec. 2008;60(4):470-512. doi: 10.1124/pr.108.000604. Epub Dec. 12, 2008, American Society for Pharmacology and Experimental Therapeutics, Bethesda, MD.

Nauck, Ma et al., "Lack of effect of synthetic human gastric inhibitory polypeptide and glucagon-like peptide 1 [7-36 amide] infused at near-physiological concentrations on pentagastrin-stimulated gastric acid secretion in normal human subjects," Digestion. 1992;52(3-4):214-21, Karger, Basel, Switzerland.

International Search Report (ISR) for PCT/JP2015/056603; I.A. fd Mar. 6, 2015, dated May 26, 2015 from the Japan Patent Office, Tokyo, Japan.

International Preliminary Report on Patentability (IPRP), Chapter I of the Patent Cooperation Treaty, including the Written Opinion for PCT/JP2015/056603; I.A. fd Mar. 6, 2015, dated Sep. 27, 2016, by the International Bureau of WIPO, Geneva, Switzerland.

Syamsunarno, Mas RAA "Fatty Acid Binding Protein-4 and -5 are Expressed in Intestinal Capillary Endothelial Cells and Regulate Lipid Absorption," Circulation Journal Feb. 20, 2014;78(Supplement 1):1737, Abstract PE-360, 78$^{th}$ Annual Scientific Meeting of the Japanese Circulation Society Abstracts, Japanese Circulation Society, Kyoto, Japan.

Furuhashi, M "Fatty Acid-Binding Protein Family," Journal of Japan Society for the Study of Obesity, Dec. 25, 2013;19(3):167-174, Nihon Himan Gakkai, Tokyo, Japan.

Comerford, KB et al., "The effects of weight loss on FABP4 and RBP4 in obese women with metabolic syndrome," Horm Metab Res. Mar. 2013;46(3):224-231. doi: 10.1055/s-0033-1353204, Epub Aug. 26, 2013, Stuttgart, Thieme, Germany.

Lan, H et al., "Small-molecule inhibitors of FABP4/5 ameliorate dyslipidemia but not insulin resistance in mice with diet-induced obesity," J Lipid Res. Apr. 2011;52(4):646-656. doi: 10.1194/jlr. M012757, Epub Feb. 4, 2011, American Society for Biochemistry and Molecular Biology, Bethesda, MD.

Song, DH et al., "Glucose-dependent insulinotropic polypeptide enhances adipocyte development and glucose uptake in part through Akt activation," Gastroenterology. Dec. 2007;133(6):1796-1805, Epub Sep. 14, 2014, W.B. Saunders, United States.

Ugleholdt, R et al., "Transgenic rescue of adipocyte glucose-dependent insulinotropic polypeptide receptor expression restores high fat diet-induced body weight gain," J Biol Chem. Dec. 30, 2011;286(52):44632-45. doi: 10.1074/jbc.M111.311779, Epub Oct. 25, 2011, American Society for Biochemistry and Molecular Biology, Bethesda, MD.

Shibue, K et al., "FABP5 is an essential modulator of fatty acid-induced GIP secretion in enteroendocrine K cells," Diabetologia, Sep. 2014;57(1):766 (Supplement).

Shibue, K et al., "Fatty acid binding protein 5(FABP5) participates in control of the fat inductivity GIP secretion in the K cell," ("Shibosan Ketsugo Tanpaku 5 (FABP5) wa K Saibo ni Kan'yo suru"), 29th Japan Society of Experimental Diabetes and Obesity on Diagnosis of Diabetes Mellitus in Animal Models (Koen Yoshishu) Program & Abstracts, Feb. 19, 2015; p. 48, Kyoto, Japan.

Smathers, RL and Petersen, DR "The human fatty acid-binding protein family: evolutionary divergences and functions," Hum Genomics. Mar. 2011;5(3):170-191, BioMed Central, England.

Furuhashi, M and Hotamisligil, GS "Fatty acid-binding proteins: role in metabolic diseases and potential as drug targets," Nat Rev Drug Discov. Jun. 2008;7(6):489-503. doi: 10.1038/nrd2589, Nature Pub. Group, England.

Hunt, CR et al., "Adipocyte P2 gene: developmental expression and homology of 5'-flanking sequences among fat cell-specific genes," Proc Natl Acad Sci USA. Jun. 1986;83(11):3786-3790, National Academy of Sciences, United States.

Makowski, L et al., "Lack of macrophage fatty-acid-binding protein aP2 protects mice deficient in apolipoprotein E against atherosclerosis," Nat Med. Jun. 2001;7(6):699-705, Nature Publishing Company, United States.

Reese-Wagoner, A et al., "Structural properties of the adipocyte lipid binding protein," Biochim Biophys Acta. Nov. 23, 1999;1441(2-3):106-116, Elsevier Pub. Co., Netherlands.

Smith, AJ et al., "Interaction of the adipocyte fatty acid-binding protein with the hormone-sensitive lipase: regulation by fatty acids and phosphorylation," J Biol Chem. Nov. 2, 2007;282(44):32424-32432, Epub Sep. 4, 2007, American Society for Biochemistry and Molecular Biology, United States.

Ogawa, E et al., "Epidermal FABP (FABP5) regulates keratinocyte differentiation by 13(S)-HODE-mediated activation of the NF-κB signaling pathway," J Invest Dermatol. Mar. 2011;131(3):604-612. doi: 10.1038/jid.2010.342, Epub Nov. 11, 2011, Elsevier, United States.

Kitanaka, N et al., "Epidermal-type fatty acid binding protein as a negative regulator of IL-12 production in dendritic cells," Biochem Biophys Res Commun. Jun. 23, 2006;345(1):459-466, Epub May 2, 2006, Elsevier, United States.

Makowski, L et al., "The fatty acid-binding protein, aP2, coordinates macrophage cholesterol trafficking and inflammatory activity. Macrophage expression of aP2 impacts peroxisome proliferator-activated receptor gamma and IkappaB kinase activities," J Biol Chem. Apr. 1, 2005;280(13):12888-12895, Epub Jan. 31, 2005, American Society for Biochemistry and Molecular Biology, United States.

Hotamisligil, GS et al., "Uncoupling of obesity from insulin resistance through a targeted mutation in aP2, the adipocyte fatty acid binding protein," Science. Nov. 22, 1996;274(5291):1377-1379, American Association for the Advancement of Science, United States.

Uysal, KT et al., "Improved glucose and lipid metabolism in genetically obese mice lacking aP2," Endocrinology. Sep. 2000;141(9):3388-3396, Oxford University Press, United States.

Maeda, K et al., "Role of the fatty acid binding protein mall in obesity and insulin resistance," Diabetes. Feb. 2003;52(2):300-307 American Diabetes Association, United States.

Maeda, K et al., "Adipocyte/macrophage fatty acid binding proteins control integrated metabolic responses in obesity and diabetes," Cell Metab. Feb. 2005;1(2):107-119, Cell Press, United States.

Cao, H et al., "Regulation of metabolic responses by adipocyte/macrophage Fatty Acid-binding proteins in leptin-deficient mice," Diabetes. Jul. 2006;55(7):1915-1922, American Diabetes Association, United States.

Boord, JB et al., "Combined adipocyte-macrophage fatty acid-binding protein deficiency improves metabolism, atherosclerosis, and survival in apolipoprotein E-deficient mice," Circulation. Sep. 14, 2004;110(11):1492-1498, Epub Sep. 7, 2004, Lippincott Williams & Wilkins, United States.

Shaughnessy, S et al., "Adipocyte metabolism in adipocyte fatty acid binding protein knockout mice (aP24$^{-/-}$) after short-term high-fat feeding: functional compensation by the keratinocyte [correction of keritinocyte] fatty acid binding protein," Diabetes. Jun. 2000;49(6):904-911, American Diabetes Association, United States.

Hertzel, AV et al., "Lipid metabolism and adipokine levels in fatty acid-binding protein null and trasgenic mice," Am J Physiol Endcrinol Metab. May 2006;29(5):E814-E823, Epub Nov. 22, 2005, American Physiological Society, United States.

Furuhashi, M et al., "Treatment of diabetes and atherosclerosis by inhibiting fatty-acid-binding protein aP2," Nature. Jun. 21, 2007;447(7147):959-965, Epub Jun. 6, 2007, Nature Publishing Group, England.

Lan, H et al., "Small-molecule inhibitors of FABP4/5 ameliorate dyslipidemia but not insulin resistance in mice with diet-induced obesity," J Lipid Res. Apr. 2011;52(4):646-656. doi: 10.1194/jlr. M012757, Epub Feb. 4, 2011, American Society for Biochemistry and Molecular Biology, United States.

[Figure 1]
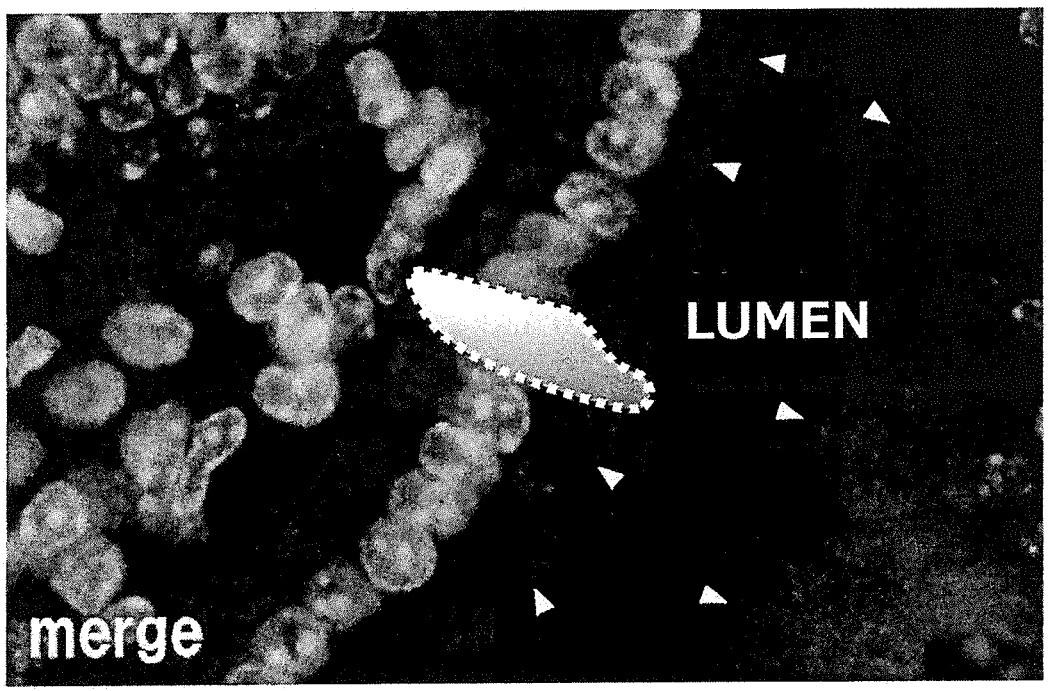

[Figure 2]
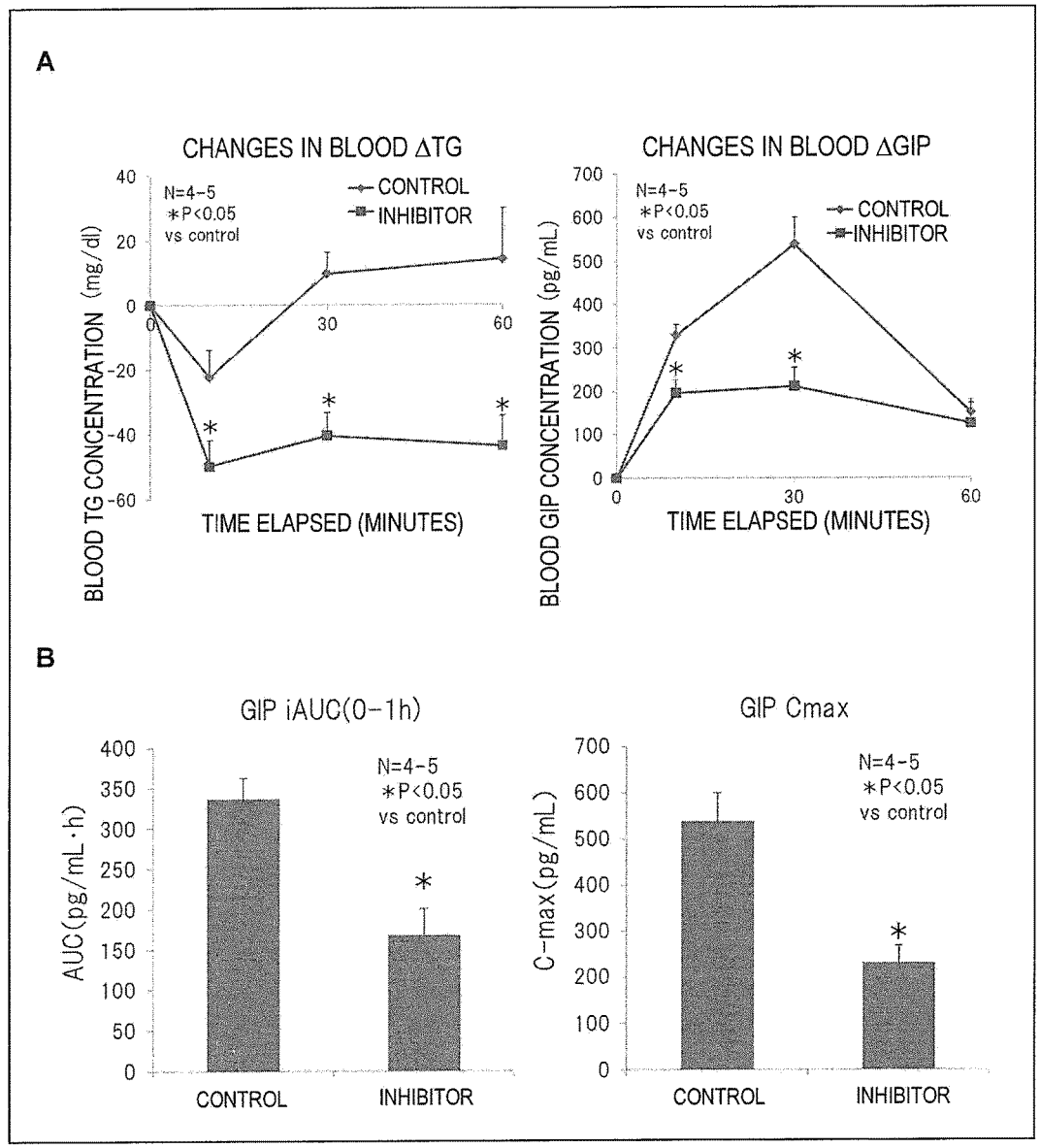

[Figure 3]
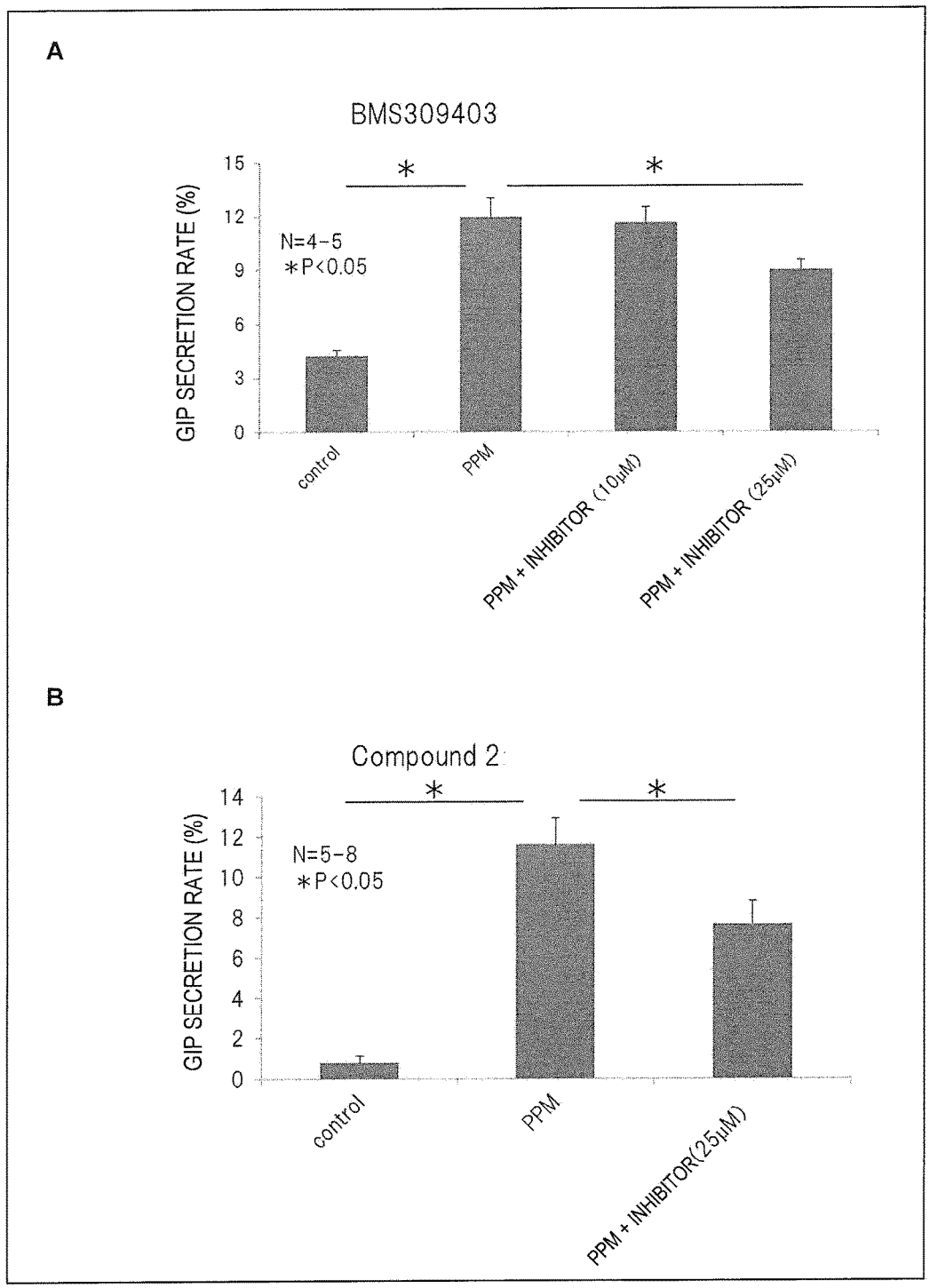

[Figure 4]
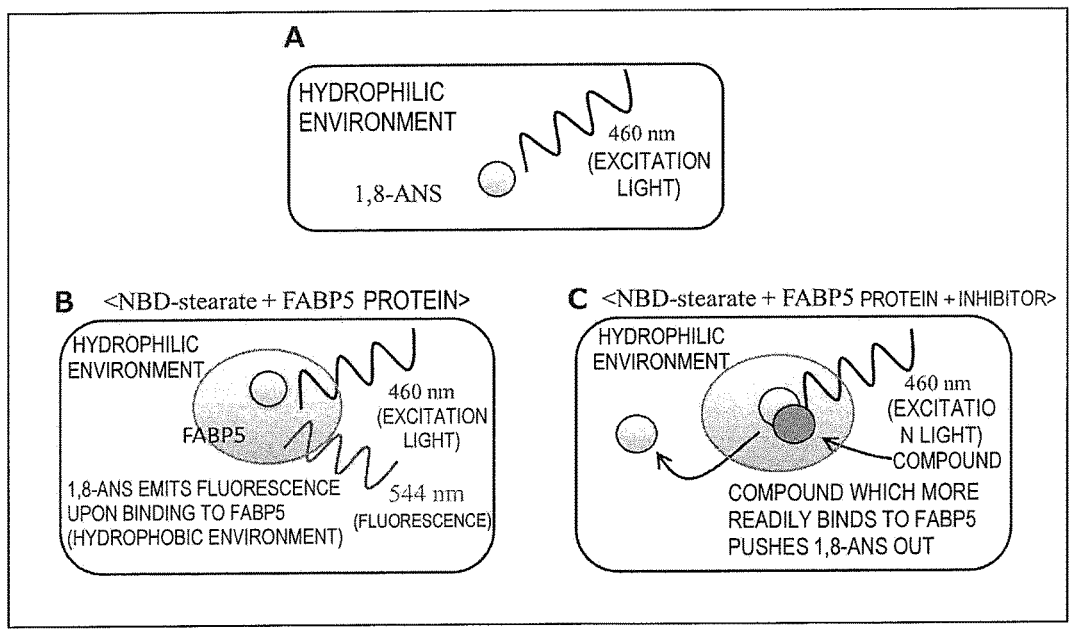

[Figure 5]
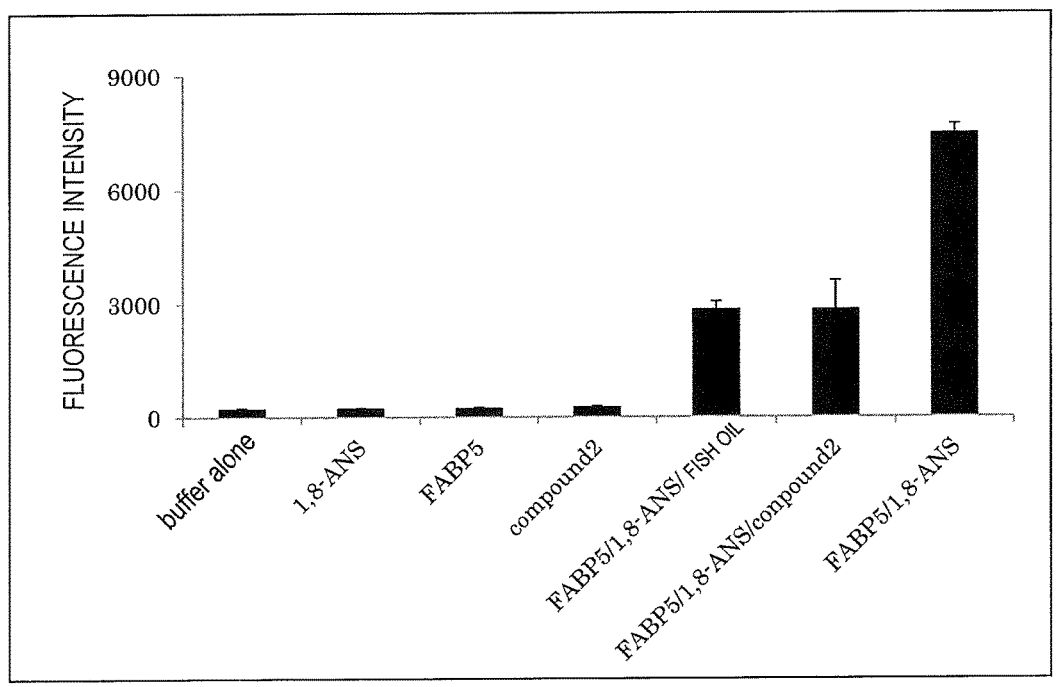

[Figure 6]
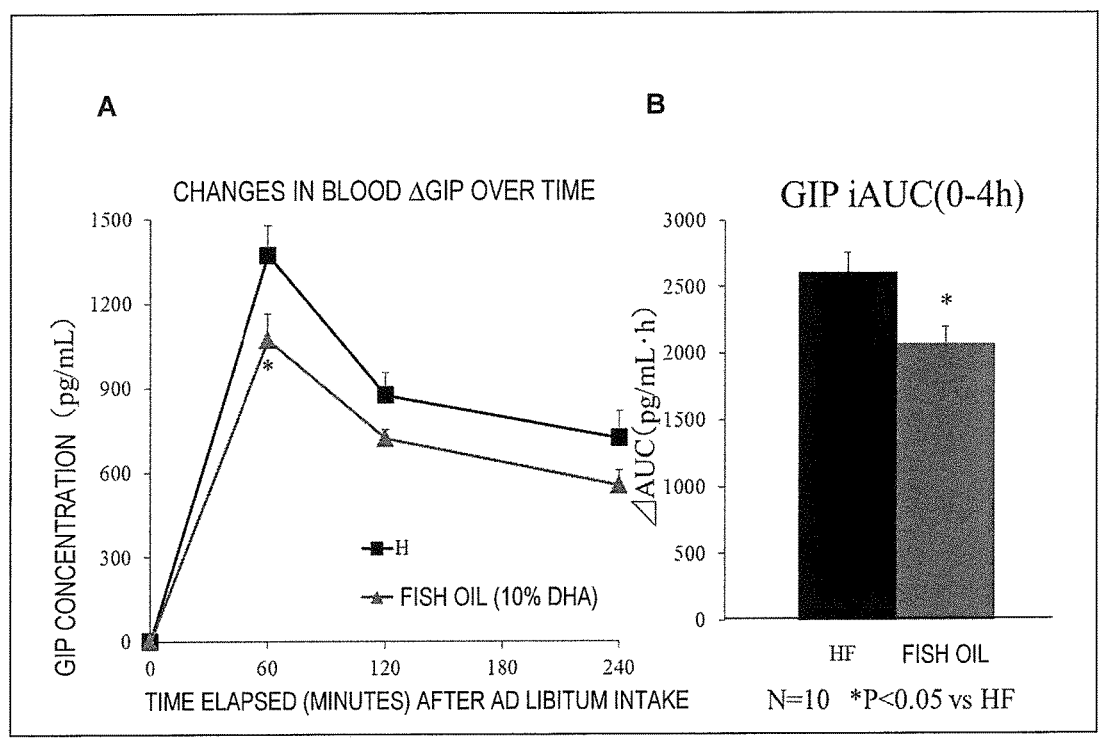

METHOD FOR EVALUATING OR SELECTING AGENT FOR SUPPRESSING GIP LEVEL ELEVATION

FIELD OF THE INVENTION

The present invention relates to a method for evaluating or selecting an agent for suppressing GIP level elevation.

BACKGROUND OF THE INVENTION

Glucose-dependent insulinotropic polypeptide (GIP) is an incretin secreted by secretory cells of the gastrointestinal epithelium (K cells) in response to the intake of lipids, carbohydrates, and amino acids. GIP promotes insulin secretion from pancreatic β cells in a glucose-dependent manner, thereby contributing to the regulation of blood glucose levels. Recently, mice with artificially elevated blood GIP concentrations are reported to have exhibited suppressed fat burning when given a high-fat diet. In addition, it has been revealed that GIP receptor-deficient mice exhibit suppressed visceral and subcutaneous fat accumulation induced by a high-fat diet. From these findings, the postprandial GIP regulation is considered to be effective for the prevention and amelioration of obesity. Further, GIP is known to have suppressing actions on gastric acid secretion and gastric motility; therefore, suppression of GIP level elevation is assumed to be effective for promoting digestion after meal and ameliorating heavy feeling in stomach. In light of the foregoing, there is a demand for the development of a substance which suppresses GIP level elevation. To accomplish this, there is a demand for the development of a rapid and highly sensitive method to evaluate the capacity of a substance to suppress GIP level elevation.

As a conventional method for evaluating or selecting an agent for suppressing GIP level elevation, a method using the expression of the CPT1 gene and CPT1 protein, or the activity of the CPT1 protein in cells as the index (Patent Literature 1), a method using the expression of the FAT/CD36 gene or FAT/CD36 protein as the index (Patent Literature 2), and the like are known.

Fatty acid-binding proteins (FABPs) are the members of the intracellular fatty acid-binding protein family, and are 14 to 15 kDa proteins having high binding affinity to fatty acids (Non Patent Literatures 1 and 2). Fatty acids exhibit various functions in cells such as the energy source and signaling molecules in metabolic regulation. FABPs enable transport of insoluble fatty acids to various organelles by binding to them, thereby playing an important role in the functional expression of fatty acids.

FABP4 and FABP5, which are isoforms of FABPs, are highly homologous in their amino acid sequences and steric structures, and are co-expressed in adipocytes and macrophages (Non Patent Literatures 2 to 4). Functional analyses of FABP4 and FABP5 have been conducted using knockout mice (Non Patent Literatures 2 to 15). FABP4 accounts for 1 to 3% of cytosolic proteins in adipocytes, and is widely used as a differentiation marker of adipocytes (Non Patent Literature 5). It is reported that FABP4 not only functions as a molecular chaperone in adipocytes, but also is involved in lipid-mediated signal transduction, responses in organelles, and further, inflammatory responses in macrophages (Non Patent Literatures 2, 6, and 9). FABP5 is suggested to be associated with the formation of psoriatic lesions in keratinocytes (Non Patent Literature 7) and is reported to be associated with the regulation of a cytokine (IL-12p70), which is a key molecule of the innate immune response in the spleen (Non Patent Literature 8).

In the ob/ob mouse, which is the type-II diabetes model, in which FABP4 was knocked out, a decrease in insulin sensitivity was suppressed (Non Patent Literature 11). Compared to the wild type, a decrease in insulin sensitivity was suppressed while there was no impact on the body weight gain and fatty liver in FABP4-knockout mice on a high-fat diet (Non Patent Literatures 4 and 10). Since the expression of FABP5 is increased in adipocytes of FABP4-knockout mice, FABP5 is considered to work in a compensatory manner (Non Patent Literatures 16 and 17). FABP5-knockout mice also show a similar tendency to FABP4-knockout mice (Non Patent Literature 12). In light of the results obtained with single-knockout mice, FABP4/5 double knockout was analyzed. As a result, compared to the wild type, the induction of diet-induced obesity, insulin resistance, type-II diabetes, and fatty liver is reported to have been suppressed in double-knockout mice on a high-fat diet (Non Patent Literatures 13, 14, and 15).

Amelioration in the pathological condition was observed in the mouse model of type-II diabetes or arteriosclerosis receiving the oral administration of BMS309403, which is an FABP inhibitor (Non Patent Literature 18). Administration of an FABP4/5 inhibitor to diet-induced obese mice resulted in amelioration in dyslipidemia, which was observed as, for example, a decrease in the blood triglyceride and free fatty acid levels (Non Patent Literature 19).

However, given that FABP2 is the type of FABP predominantly expressed in the intestine, it has been conventionally believed that FABP2 plays a role in lipid metabolism in the intestine.

CITATION LIST

[Patent Literature 1] JP-A-2011-080804
[Patent Literature 2] JP-A-2011-080803
[Non Patent Literature 1] Hum. Genomics, 2011, 5: 170 to 191
[Non Patent Literature 2] Nat. Rev. Drug Discov., 2008, 7: 489 to 503
[Non Patent Literature 3] Proc. Natl. Acad. Sci. U.S.A, 1986, 83: 3786 to 3790
[Non Patent Literature 4] Nat. Med., 2001, 7: 699 to 705
[Non Patent Literature 5] Biochim. Biophys. Acta., 1999, 1441: 106 to 116.
[Non Patent Literature 6] J. Biol. Chem., 2007, 282: 32424 to 32432.
[Non Patent Literature 7] J. Invest. Dermatol., 2011, 131: 604 to 612
[Non Patent Literature 8] Biochem. Biophys. Res. Commun., 2006, 345: 459 to 466
[Non Patent Literature 9] J. Biol. Chem., 2005, 280: 12888 to 12895
[Non Patent Literature 10] Science, 1996, 274: 1377 to 1379
[Non Patent Literature 11] Endocrinology, 2000, 141: 3388 to 3396
[Non Patent Literature 12] Diabetes, 2003, 52: 300 to 307
[Non Patent Literature 13] Cell Metab., 2005, 1: 107 to 119
[Non Patent Literature 14] Diabetes, 2006, 55: 1915 to 1922
[Non Patent Literature 15] Circulation, 2004, 110: 1492 to 1498
[Non Patent Literature 16] Diabetes, 2000, 49: 904 to 911
[Non Patent Literature 17] Am. J. Physiol. Endocrinol. Metab., 2006, 290: E814 to E823
[Non Patent Literature 18] Nature, 2007, 447: 959 to 965

[Non Patent Literature 19] J. Lipid Res., 2011, 52: 646 to 656

SUMMARY OF THE INVENTION

The present invention provides a method for evaluating or selecting an agent for suppressing GIP level elevation, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as an agent for suppressing GIP level elevation based on results of the above (C).

The present invention also provides a method for evaluating or selecting an agent for suppressing GIP level elevation, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as an agent for suppressing GIP level elevation based on results of the above (C').

BRIEF DESCRIPTION OF THE DRAWINGS

FIG. 1 illustrates co-immunostaining of FABP5 and GIP in intestinal cells.

FIG. 2 illustrates the blood TG and GIP concentrations in mice after single-dose administration of lipid emulsions, in which FIG. 2A shows changes in blood ΔTG and ΔGIP over time and FIG. 2B shows the iAUC (0-1 h) and Cmax of the blood GIP concentration.

FIG. 3 illustrates the effects of FABP4/5 inhibitors on lipid-induced GIP secretion in the primary culture cells of the small intestine, in which FIG. 3A shows the effects of BMS309403 and FIG. 3B shows the effects of Compound 2.

FIG. 4 illustrates the principle of a method for measuring the activity of FABP5 used in Example 4.

FIG. 5 illustrates the inhibitory activities of GIP level elevation suppressing substances on FABP5.

FIG. 6 illustrates the suppressing action of fish oil on GIP level elevation, in which FIG. 6A shows the amount of changes in the blood GIP concentration (ΔGIP) over time and FIG. 6B shows the iAUC (0-4 h) of the blood GIP concentration. *:P<0.05.

DETAILED DESCRIPTION OF THE INVENTION

The present invention relates to a method for evaluating or selecting an agent for suppressing GIP level elevation.

The present inventors found that FABP4 and FABP5 (they may be collectively expressed as FABP4/5 in the present specification) were expressed in GIP-secreting intestinal cells, and that the blood GIP concentration was reduced by inhibiting the aforementioned FABP4/5, and therefore, that a substance which inhibits FABP4/5 was useful as an agent for suppressing GIP level elevation. Based on these findings, the present inventors found that an agent for suppressing GIP level elevation could be evaluated or selected using the inhibitory action on the expression or activity of FABP4/5 as an index.

According to the present invention, the suppressing effects of various substances on GIP level elevation can be evaluated more simply and correctly, thereby enabling the selection of an excellent agent for suppressing GIP level elevation. Also, an agent for suppressing GIP level elevation selected by the method of the present invention is useful as an active ingredient for lowering the possibility of developing obesity and the like, preventing or ameliorating obesity and the like, preventing body weight gain, lowering the body weight, promoting digestion after meal, or ameliorating heavy feeling in stomach.

It has already been known that FABPs are expressed in the intestine and that FABP4 is localized in the membrane of the intestinal gland epithelial cells by immunostaining of the tissue specimens prepared from the mouse intestinal tract ([www.rndsystems.com/ihc_molecule_images.aspx?m=1416]). Meanwhile, it has been conventionally known that FABP2 is the type of FABP predominantly expressed in the intestine, and therefore, FABP2 has been believed to play a role in lipid metabolism in the intestine.

However, when the present inventors conducted co-immunostaining of GIP and FABP5 in the tissue specimens prepared from the intestinal tract, they observed an intense signal for FABP5 in the cells in which a signal for GIP was detected (FIG. 1). The above results revealed that both FABP4/5 were proteins expressed in the intestinal epithelial cells. As will be shown in the Examples to be described later, the GIP concentration was reduced by inhibiting FABP4/5, which revealed that FABP4/5 were involved in the secretion of GIP. In light of the above, a substance which inhibits FABP4/5 is useful as an agent for suppressing GIP level elevation, and the suppressing effects of various substances on GIP level elevation can be evaluated and an agent for suppressing GIP level elevation can be selected by measuring the expression levels of the FABP4/5 genes or the expression levels or activities of the FABP4/5 proteins.

Accordingly, in the present invention, the suppressing actions of various substances on GIP level elevation are evaluated using the inhibitory actions on FABP4/5 as an index, and based on the evaluation results obtained, agents for suppressing GIP level elevation are selected. According to the present specification, the phrase "suppression of GIP level elevation" means to suppress an increase in GIP secreted from K cells present in the small intestine in response to the ingestion of a meal containing fats and carbohydrates, particularly fats, more particularly, triacylglycerol. That is, according to the present specification, the phrase "suppression of GIP level elevation" mainly means to suppress the GIP increase occurring after meal. Further, according to the present specification, the phrase "suppressing action on GIP level elevation" is a concept encompassing both the suppressing action on the secretion of GIP, which means to suppress GIP level elevation by suppressing the secretion of GIP from K cells, and GIP-lowering action, which means to suppress GIP level elevation by lowering the blood GIP concentration.

According to the present specification, the term "expression of FABP4/5" means the expression of the FABP4 gene or FABP5 gene, or the expression of the FABP4 protein or FABP5 protein. Also, according to the present specification, the term "activity of FABP4/5" means the activity of the FABP4 protein or FABP5 protein.

The method for evaluating or selecting an agent for suppressing GIP level elevation of the present invention can be carried out in vitro, ex vivo, or in vivo.

When the method for evaluating or selecting an agent for suppressing GIP level elevation of the present invention is carried out in vitro or ex vivo, the method comprises the following steps (A) to (D):
(A) contacting a test substance with a mammal-derived tissue or cell capable of expressing FABP4/5;
(B) measuring an expression level or activity of FABP4/5 in the mammal-derived tissue or cell;
(C) comparing the expression level or activity measured in the above (B) with an expression level or activity of FABP4/5 in a control group; and
(D) evaluating or selecting a test substance which reduces the expression level or activity of FABP4/5 as an agent for suppressing GIP level elevation based on results of the above (C).

A test substance used in the method of the present invention described above is not particularly limited as long as it is a substance which is desired to be used as an agent for suppressing GIP level elevation. The test substance can be a naturally occurring substance or a substance artificially synthesized by a chemical or biological method, etc., and further, the test substance can be a compound, composition, or mixture.

Examples of the mammal-derived tissue or cell capable of expressing FABP4/5 used in the aforementioned step (A) include a tissue or cell expressing the FABP4 gene or FABP5 gene, or the FABP4 protein or FABP5 protein isolated from mammals, or a culture of such a tissue or cell. Examples of the isolated tissue or cell or the culture of such a tissue or cell include a tissue or cell of the small intestine such as the duodenum and jejunum collected from mammals, an adipose tissue or cell, a thymic epithelial tissue or cell, a skin epithelial tissue or cell, and a culture of these tissues or cells; a primary culture cell of the small intestine; a cultured cell of the small intestine such as a Caco-2 cell, an IEC-6 cell, an IEC-18 cell, a STC-1 cell, and a GLUTag cell; and a 3T3-L1 cell.

Alternatively, examples of the mammal-derived tissue or cell capable of expressing FABP4/5 used in the aforementioned step (A) include a mammal-derived tissue or cell genetically modified to express the FABP4 gene or FABP5 gene, or the FABP4 protein or FABP5 protein, or a culture of such a tissue or cell. The genetically modified mammal-derived tissue or cell or the culture of such a tissue or cell can be produced by, for example, transforming an arbitrary tissue or cell of mammals so that the tissue or cell expresses FABP4/5 or the expression of FABP4/5 is enhanced by introducing a gene encoding the FABP4 protein or FABP5 protein into the tissue or cell. Examples of a method for introducing a gene into cells include, but are not limited to, electroporation and vector-mediated gene transfer such as lipofection.

Examples of a mammal from which a tissue or cell capable of expressing FABP4/5 used in the method of the present invention is obtained include, but are not particularly limited to, a human, a mouse, a rat, a hamster, and a rabbit.

The test substance can be contacted with the aforementioned mammal-derived tissue or cell capable of expressing FABP4/5 by, for example, adding the test substance to a culture solution in advance so as to achieve the desired concentration, and then placing the tissue or cell in the culture solution, or adding the test substance to a culture solution containing the tissue or cell so as to achieve the desired concentration. It is preferable to culture the tissue or cell after contact, for example, at room temperature (25° C.) to 37° C. normally for about from 3 to 48 hours, preferably for about from 6 to 24 hours.

The seeding density of the aforementioned tissue or cell in the aforementioned culture solution is not particularly limited as long as it is such a density that allows the growth of cells. The addition concentration of the test substance is preferably from 0.00001 to 10% by mass (dry residue), particularly preferably from 0.0001 to 3% by mass (dry residue).

As the culture medium used for the aforementioned tissue or cell, an ordinary medium can be used, and examples thereof include 10% FBS-containing Dulbecco's Modified Eagle's Medium. It is preferable to add a growth supplement such as serum, a growth factor, and insulin, an antibiotic, and the like to the medium at the time of cell passage or cell growth.

Next, in the step (B), the aforementioned tissue or cell is collected and the expression level of the FABP4 gene or FABP5 gene, the expression level of the FABP4 protein or FABP5 protein, or the activity of the FABP4 protein or FABP5 protein is measured. When the gene expression level is detected on the mRNA level, the measurement can be conducted by, for example, extracting the total RNA from cells and detecting and quantitating mRNA transcribed from the FABP4/5 genes using real-time RT-PCR, RNase protection assay, Northern blot, and the like.

The expression level of the FABP4/5 proteins can be measured by routine immunoassay such as RIA, EIA, ELISA, bioassay, and Western blot, of which Western blot is desired for its inexpensiveness and simplicity. The activity of the FABP4/5 proteins can be measured by, for example, measuring the binding amount of substrates bound to the FABP4/5 proteins.

In the steps (C) and (D), the expression level or activity of FABP4/5 in the mammal-derived tissue or cell capable of expressing FABP4/5 which have been contacted with the test substance (test group) measured in the aforementioned step (B) is compared with the expression level or activity of FABP4/5 in a control group, and based on the results of comparison thus obtained, a test substance which can be used as an agent for suppressing GIP level elevation is selected.

Examples of the control group include the same mammal-derived tissue or cell capable of expressing FABP4/5 as that used in the test group, except for being contacted with the test substance. Alternatively, examples of the control group include a mammal-derived tissue or cell naturally incapable or almost incapable of expressing FABP4/5; the same tissue or cell as that used in the test group which is modified so as not to express FABP4/5; and further, the same tissue or cell as that used in the test group which is modified so as not to express FABP4/5 and is contacted with the test substance. Examples of the tissue or cell which is modified so as not to express FABP4/5 include a cell in which FABP4/5 are knocked down by siRNA and a tissue or cell derived from an FABP4/5 knockout mouse. The expression level or activity of FABP4/5 in the control group can be measured by the same procedure as that used in the test group as explained in connection with the aforementioned step (B).

Next, the expression level or activity of FABP4/5 in the test group is compared with the expression level or activity of FABP4/5 in the control group. When the expression level or activity in the test group is reduced compared to the control group, the relevant test substance is evaluated as having a suppressing effect on GIP level elevation, and accordingly, selected as an agent for suppressing GIP level elevation. For example, when the expression level or activity in the test group is statistically significantly reduced compared to the expression level or activity in the control group, the relevant test substance is evaluated as having a suppressing effect on GIP level elevation. As another example, when the expression level or activity in the test group is 90% or less, preferably 80% or less, more preferably 60% or less taking the expression level or activity in the control group as 100%, the relevant test substance is evaluated as having a suppressing effect on GIP level elevation. A test substance which is evaluated as having a suppressing effect on GIP level elevation is selected as an agent for suppressing GIP level elevation.

When the method for evaluating or selecting an agent for suppressing GIP level elevation of the present invention is conducted in vivo, the method comprises the following steps (A') to (D'):
(A') administering a test substance to a non-human mammal;
(B') measuring an expression level or activity of FABP4/5 in a small intestine collected from the non-human mammal;
(C') comparing the expression level or activity measured in the above (B') with an expression level or activity of FABP4/5 in a small intestine collected from a non-human mammal in a control group; and
(D') evaluating or selecting a test substance which reduces the expression level or activity of FABP4/5 as an agent for suppressing GIP level elevation based on results of the above (C').

The non-human mammal used in the aforementioned step (A') can be any kind of animal, regardless of sex and age. Examples include a mouse, a rat, a hamster, a guinea pig, a rabbit, a cat, a dog, and primates such as a monkey. From the viewpoint of accessibility and ease of handling, rodents such as a rat and a mouse are preferable.

Examples of a method of administering a test substance to the aforementioned non-human mammal include oral administration, gastrointestinal administration, intraperitoneal administration, intravascular administration, intradermal administration, and subcutaneous administration. From the viewpoint of simplicity and low invasiveness, a method of oral administration is preferable. Alternatively, in light of the fact that GIP is secreted by K cells in the duodenum and jejunum, it is also preferable to directly circulate the test substance through the duodenum and jejunum by cannulation and the like.

The dosage of the test substance is from 0.0004 mg/g body weight or more, preferably from 0.04 to 2 mg/g body weight. As to the number of administration, the test substance can be administered as a single dose or in divided doses at intervals. The test substance is preferably administered at every meal, more preferably administered during 60 minutes before meal to 60 minutes after meal.

Next, in the step (B'), the expression level or activity of FABP4/5 in the small intestine of the non-human mammal administered with the test substance is measured. The method of measurement is not particularly limited and may be an invasive or noninvasive method.

For example, the small intestine is collected from the aforementioned non-human mammal from 1 to 360 minutes, preferably from 5 to 120 minutes after the administration of the test substance. As to the collection of the small intestine, the animal is subjected to a laparotomy to collect the part below the pylorus of the stomach under anesthesia or immediately after euthanasia. Subsequently, the expression level or activity of FABP4/5 in the cells collected is measured.

In the steps (C') and (D'), the expression level or activity of FABP4/5 in the small intestine of the non-human mammal administered with the test substance obtained as above (test group) is compared with the expression level or activity in the small intestine collected from the same non-human mammal which is not administered with the test substance (control group). When the expression level or activity in the test group is reduced compared to that in the control group, the test substance is evaluated as having a suppressing effect on GIP level elevation and selected as an agent for suppressing GIP level elevation.

Other techniques used in the present method, for example, the kind of test substance which can be used, the procedure for measuring the expression level or activity of FABP4/5, the procedure for comparing the test group and the control group, and the procedure for evaluating or selecting a test substance, are the same as those used in the in vitro or ex vivo method described above.

The substance thus selected can further be screened as needed. For example, with respect to the test substance which is evaluated as having an suppressing effect on GIP level elevation or selected by the aforementioned method, the capability thereof to suppress GIP level elevation from K cells is directly measured by a secretion stimulation test using a cultured cell line of the mammalian small intestine K cell model or by a single administration experiment using laboratory animals, whereby a substance having a more potent suppressing action on GIP level elevation can further be selected.

The agent for suppressing GIP level elevation selected by the present invention in accordance with the procedure described as above reduces postprandial GIP after meal and is used as an active ingredient for lowering the possibility of developing obesity, preventing or ameliorating obesity, suppressing body weight loss or gain, promoting digestion, or ameliorating heavy feeling in stomach.

In light of the above, according to another embodiment, the present invention provides a method for evaluating or selecting an appetite suppressant, comprising the aforementioned steps (A) to (D) or (A') to (D'). According to yet another embodiment, the present invention provides a method for evaluating or selecting an agent for preventing and/or ameliorating obesity, comprising the aforementioned steps (A) to (D) or (A') to (D'). According to yet another embodiment, the present invention provides a method for evaluating or selecting a body weight gain suppressant, comprising the aforementioned steps (A) to (D) or (A') to (D'). According to yet another embodiment, the present invention provides a method for evaluating or selecting a digestion promoter or an agent for ameliorating heavy feeling in stomach, comprising the aforementioned steps (A) to (D) or (A') to (D').

In the step (D) or (D') of these methods, the test substance which reduces the expression level or activity of FABP4/5 is evaluated or selected as an appetite suppressant, an agent for preventing and/or ameliorating obesity, a body weight gain suppressant, or a digestion promoter or an agent for ameliorating heavy feeling in stomach based on the results of the step (C) or (C').

The following compositions, production methods, usage, or methods are disclosed in the present specification as exemplary embodiments of the present invention. However, the present invention is not limited to the following embodiments.

<1> A method for evaluating or selecting an agent for suppressing GIP level elevation, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as an agent for suppressing GIP level elevation based on results of the above (C).

<2> A method for evaluating or selecting an appetite suppressant, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as an appetite suppressant based on results of the above (C).

<3> A method for evaluating or selecting an agent for preventing and/or ameliorating obesity, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as an agent for preventing and/or ameliorating obesity based on results of the above (C).

<4> A method for evaluating or selecting a body weight gain suppressant, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as a body weight gain suppressant based on results of the above (C).

<5> A method for evaluating or selecting a digestion promoter, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as a digestion promoter based on results of the above (C).

<6> A method for evaluating or selecting an agent for ameliorating heavy feeling in stomach, comprising the following steps (A) to (D):
(A) contacting a test substance with a mammal-derived tissue or cell capable of expressing an FABP4 gene or FABP5 gene, or an FABP4 protein or FABP5 protein;
(B) measuring an expression level of the FABP4 gene or FABP5 gene, an expression level of the FABP4 protein or FABP5 protein, or an activity of the FABP4 protein or FABP5 protein in the mammal-derived tissue or cell;
(C) comparing the expression level or activity measured in the above (B) with an expression level of an FABP4 gene or FABP5 gene, an expression level of an FABP4 protein or FABP5 protein, or an activity of an FABP4 protein or FABP5 protein in a control group; and
(D) evaluating or selecting a test substance which reduces the expression level of the FABP4 gene or FABP5 gene, the expression level of the FABP4 protein or FABP5 protein, or the activity of the FABP4 protein or FABP5 protein as an agent for ameliorating heavy feeling in stomach based on results of the above (C).

<7> The method according to any one of <1> to <6>, wherein the mammal-derived tissue or cell capable of expressing an FABP4 gene or FABP5 gene, or an FABP4 protein or FABP5 protein is any of the followings:
(1) a tissue or cell of a small intestine collected from a mammal, or a culture of the tissue or cell;
(2) an adipose tissue or cell, a thymic epithelial tissue or cell, a skin epithelial tissue or cell collected from a mammal, or a culture of these tissues or cells;
(3) a mammal-derived tissue or cell genetically modified to express an FABP4 gene or FABP5 gene, or an FABP4 protein or FABP5 protein, or a culture of the tissue or cell;
(4) a primary culture cell of a small intestine; and
(5) a Caco-2 cell, an IEC-6 cell, an IEC-18 cell, a STC-1 cell, a GLUTag cell, or a 3T3-L1 cell.
<8> Preferably the method according to any one of <1> to <7>, wherein the control is preferably any of the followings:
(1) the mammal-derived tissue or cell capable of expressing an FABP4 gene or FABP5 gene, or an FABP4 protein or FABP5 protein, wherein the tissue or cell is not contacted with the test substance;
(2) a mammalian-derived tissue or cell naturally incapable or almost incapable of expressing an FABP4 gene or FABP5 gene, or an FABP4 protein or FABP5 protein;
(3) the mammal-derived tissue or cell capable of expressing an FABP4 gene or FABP5 gene, or an FABP4 protein or FABP5 protein, wherein the tissue or cell is modified so as not to express the gene or protein; or
(4) the tissue or cell according to (2) or (3), wherein the tissue or cell is contacted with the test substance.
<9> The method according to any one of <1> to <8>, wherein, preferably, when the expression level or activity measured in the above (B) is statistically significantly reduced compared to the expression level or activity in the control group, the test substance is evaluated as having an suppressing effect on GIP level elevation, an appetite suppressing effect, an obesity preventing and/or ameliorating effect, an suppressing effect on body weight gain, a digestion promoting effect, or an ameliorating effect on heavy feeling in stomach.
<10> The method according to any one of <1> to <8>, wherein, preferably, when the expression level or activity measured in the above (B) is 90% or less, preferably 80% or less, more preferably 60% or less taking the expression level or activity in the control group as 100%, the test substance is evaluated as having an suppressing effect on GIP level elevation, an appetite suppressing effect, an obesity preventing and/or ameliorating effect, an inhibitory effect on body weight gain, a digestion promoting effect, or an ameliorating effect on heavy feeling in stomach.
<11> A method for evaluating or selecting an agent for suppressing GIP level elevation, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as an agent for suppressing GIP level elevation based on results of the above (C').
<12> A method for evaluating or selecting an appetite suppressant, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as an appetite suppressant based on results of the above (C').
<13> A method for evaluating or selecting an agent for preventing and/or ameliorating obesity, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as an agent for preventing and/or ameliorating obesity based on results of the above (C').
<14> A method for evaluating or selecting a body weight gain suppressant, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as a body weight gain suppressant based on results of the above (C').

<15> A method for evaluating or selecting a digestion promoter, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as a digestion promoter based on results of the above (C').
<16> A method for evaluating or selecting an agent for ameliorating heavy feeling in stomach, comprising the following steps (A') to (D'):
(A') administering a test substance to a non-human mammal;
(B') measuring an expression level of an FABP4 gene or FABP5 gene, an expression level of an FABP4 protein or FABP5 protein, or an activity of an FABP4 protein or FABP5 protein in a small intestine collected from the non-human mammal;
(C') comparing the expression level or activity measured in the above (B') with an expression level of an FABP4 gene or FABP5 gene, an expression level of an FABP4 protein or FABP5 protein, or an activity of an FABP4 protein or FABP5 protein in a small intestine collected from a non-human mammal in a control group; and
(D') evaluating or selecting a test substance which reduces the expression level of the FABP4 gene or FABP5 gene, the expression level of the FABP4 protein or FABP5 protein, or the activity of the FABP4 protein or FABP5 protein as an agent for ameliorating heavy feeling in stomach based on results of the above (C').
<17> The method according to any one of <11> to <16>, wherein, preferably, the control group is a small intestine collected from the non-human mammal, wherein the non-human mammal is not administered with the test substance.
<18> The method according to any one of <11> to <17>, wherein, preferably, when the expression level or activity measured in the above (B') is statistically significantly reduced compared to the expression level or activity in the control group, the test substance is evaluated as having an suppressing effect on GIP level elevation, an appetite suppressing effect, an obesity preventing and/or ameliorating effect, an inhibitory effect on body weight gain, a digestion promoting effect, or an ameliorating effect on heavy feeling in stomach.
<19> The method according to any one of <11> to <17>, wherein, preferably, when the expression level or activity measured in the above (B') is 90% or less, preferably 80% or less, more preferably 60% or less taking the expression level or activity in the control group as 100%, the test substance is evaluated as having an suppressing effect on GIP level elevation, an appetite suppressing effect, an obesity preventing and/or ameliorating effect, an suppressing effect on body weight gain, a digestion promoting effect, or an ameliorating effect on heavy feeling in stomach.

EXAMPLES

Hereinafter, the present invention will be more specifically described with Examples.

(FABP4/5 Inhibitors)

In the following Examples, BMS309403 (AstaTech, Inc.) or Compound 2 (J Lipid Res. 2011, 52, 646 to 656) shown below was used as the FABP4/5 inhibitor.

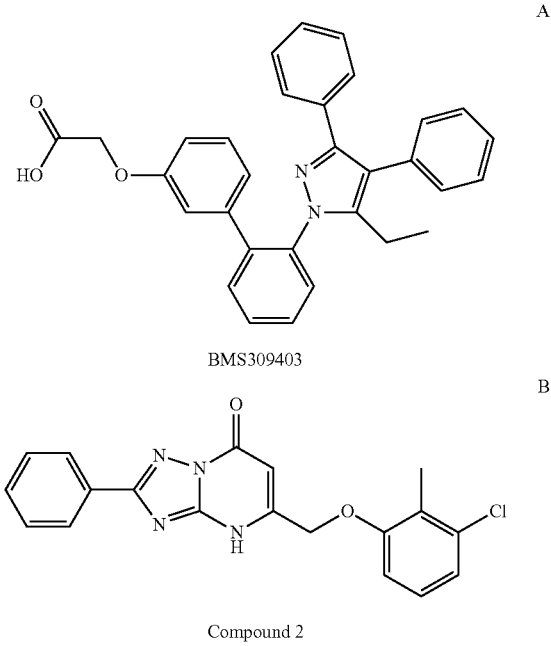

Example 1 Expression of FABP4/5 in Intestinal Cells (Immunostaining)

The duodenum collected from C57BL/6J mice (male) (CLEA Japan, Inc.) was fixed in a 4% aqueous solution of paraformaldehyde, and then frozen sections were prepared and subjected to immunostaining. Double fluorescence staining was performed using antibodies for GIP and FABP5 to examine the expression of FABP5 in intestinal cells. As the primary antibody, T-4340 (the product of Peninsula Laboratories International, Inc.) was used as an antibody for GIP and AF1476 (the product of R&D Systems, Inc.) was used as an antibody for FABP5. Also, as the secondary antibody, Alexa Fluor 488 Donkey Anti-Rabbit IgG (the product of Invitrogen) and Alexa Fluor 568 Donkey Anti-goat IgG (the product of Invitrogen) were used. In accordance with the routine procedure, samples were fixed in a 4% aqueous solution of paraformaldehyde at 4° C. for 10 minutes and then washed with PBS, and reactions with the primary antibodies (a 100-fold blocking solution: 10% Donkey Serum in PBS) were allowed to take place at room temperature for three hours. After washing with PBS again, reactions with the secondary antibodies (a 500-fold blocking solution) were allowed to take place at room temperature for one hour. After washing with PBS, Prolong Gold antifade reagent with DAPI (the product of Invitrogen) was used for nuclear staining and mounting, followed by microscopic observation (using lasers of 405 nm, 488 nm, and 568 nm).
(Results)
The staining image is shown in FIG. 1. In the mouse small intestine, FABP5 was continuously expressed along the luminal side (arrows) in the cells of the villus. Further, the expression of FABP5 was observed also in GIP-positive K cells (within the white dotted line). It should be noted that it has already been known that FABP4 is localized in the membrane of the intestinal gland epithelial cells ([www.rnd-systems.com/ihc_molecule_images.aspx?m=1416]). Therefore, the results of this Example revealed that both of FABP4/5 were expressed in the intestinal epithelial cells.

Example 2 Effects of Inhibition of FABP4/5 on the Secretion of GIP (Single-Dose Administration Test in Mice)

Mice (C57BL/6J, male, 9 weeks old, n=4 to 5, CLEA Japan, Inc.) were fasted for 18 hours and then given intragastric administration of the FABP4/5 inhibitor BMS309403 (30 mg/kg body weight) in a solvent (10% 1-methyl-2-pyrrolione, 5% cremophor, and 2% ethanol) or only the solvent (control) through feeding needles under anesthesia. After 30 minutes, intragastric administration of lipid emulsions (triolein; 2 mg/kg body weight) was given. Blood was collected from the orbital sinus before and 10, 30, and 60 minutes after the administration of lipid emulsions. The blood thus collected was centrifuged at 11,000 rpm, 4° C. for 10 minutes to prepare the plasma. The blood GIP and triglyceride (TG) concentrations were measured with a GIP ELISA kit (for rat/mouse) (Merck Millipore Corporation) and a triglyceride E-test Wako (Wako Pure Chemical Industries, Ltd.), respectively.

(Results)

The changes over time of the amount of changes in the blood TG concentration (ΔTG) and blood GIP concentration (ΔGIP) in mice after single-dose administration of lipid emulsions, and the iAUC (0-1 h) and Cmax of the blood GIP concentration are shown in FIG. 2. The increase in the blood TG and GIP concentrations after the administration of lipid emulsions was statistically significantly reduced in the inhibitor addition group compared to the control group (FIG. 2A). Further, the iAUC and Cmax of the blood GIP concentration were also statistically significantly reduced in the inhibitor addition group compared to the control group (FIG. 2B).

Example 3 FABP4/5 Inhibition Test in the Primary Culture Cells of the Small Intestine (Preparation of the Primary Culture Cells of the Small Intestine)

C57BL/6J mice, 13 to 17 weeks old, were euthanized by cervical dislocation under anesthesia. The upper part of the small intestine (up to 10 cm immediately below the pylorus) was taken out and immersed in ice-cooled L-15 media (Sigma-Aldrich Co. LLC.). The small intestine was then transferred to ice-cooled PBS. Fat, blood vessels, etc. adhering to the intestinal tract were carefully removed. The inside of the lumen was washed with ice-cooled PBS and the tissue was cut into small pieces (pieces having an area of 2 mm² or smaller) with a scalpel. The small pieces were washed three to four times with PBS, to which 10 mL of DMEM (Sigma-Aldrich Co. LLC.) having Collagenase XI (Sigma-Aldrich Co. LLC.; 0.4 mg/mL) dissolved therein was added, followed by vigorous shaking for 10 seconds and then incubation at 37° C. for five minutes. The supernatants were then removed and 10 mL of the Collagenase solution was added again, followed by vigorous shaking for 10 seconds and then incubation at 37° C. for five minutes. Thereafter, the supernatants were removed and 10 mL of the Collagenase solution was added again, followed by vigorous shaking for 10 seconds and then incubation at 37° C. for 15 minutes. During the incubation, samples were shaken for 10 seconds every five minutes. After the incubation, the supernatants were collected (supernatant 1), and similarly, the Collagenase solution was added, followed by incubation for 15 minutes. The supernatants were then collected (supernatant 2). The supernatants 1 and 2 were centrifuged at 100 rcf (approximately 800 rpm) for three minutes (at room temperature). The resulting supernatants were removed and the remaining products were each suspended in 10 mL of DMEM. The resulting suspensions were combined and centrifuged at 100 rcf for three minutes (at room temperature). The resulting supernatant was removed and the remaining product was suspended in 7 mL of DMEM (containing 10% FBS (Invitrogen), 1% Glutamax (Invitrogen), and 1% penicillin/streptomycin (Invitrogen)). The resulting suspension was seeded in 48-well plates coated with Matrigel™ (BD Biosciences) (24 wells/mouse), followed by incubation at 37° C. in 5% $CO_2$.

(GIP Secretion Stimulation)

After 24 hours of culture, the primary culture cells of the small intestine were gently washed once with stimulation media (4.5 mM KCl, 138 mM NaCl, 4.2 mM $NaHCO_3$, 1.2 mM $NaH_2PO_4$, 2.6 mM $CaCl_2$, 1.2 mM $MgCl_2$, 10 mM HEPES, and NaOH (adjusted to pH 7.4)), and the cells were incubated in stimulation media alone or with the addition of FABP4/5 inhibitors (10 or 25 μM). After 30 minutes, the cells were gently washed once with stimulation media and incubated in stimulation media alone (control) or with the addition of lipid micelles (PPM: stimulation media+500 μM sodium taurocholate, 200 μM oleic acid, and 50 μM 2-monoolein) or PPM+FABP4/5 inhibitors (10 or 25 μM). After 30 minutes, the media were collected. As the FABP4/5 inhibitor, BMS309403 or Compound 2 was used.

(Measurement of GIP Secretion Rates)

The media thus collected were centrifuged at 8,000 rpm, 4° C. for five minutes to obtain supernatants (secretion samples). A cell lysis buffer (0.5% (w/v) sodium deoxycholate monohydrate, 1% (v/v) Igepal CA-630, 50 mmoL/L Tris-HCl (pH 7.4), 150 mmol/L NaCl, and one EDTA-free protease inhibitor cocktail tablet (Roche)) was added to the plates after collection of the supernatants. After freezing and thawing, cells were collected and centrifuged at 12,000 rpm, 4° C. for five minutes to obtain supernatants (lysis samples). GIP was quantitated in these samples with a GIP ELISA kit (for rat/mouse) (Merck Millipore Corporation) to obtain GIP secretion rates. The method for calculating GIP secretion rates is shown below.

$$\text{GIP secretion rate (\%)} = \frac{\text{Amount of GIP secreted in media}}{\text{Total amount of GIP}} \times 100$$
$$= \frac{\text{Amount of GIP (Secretion sample)}}{\text{Amount of GIP (Lysis sample)} + \text{Amount of GIP (Secretion sample)}} \times 100$$

(Results)

The GIP secretion rates of the PPM-stimulated primary culture cells of the small intestine are shown in FIG. 3. Compared to the control group, the GIP secretion rate was statistically significantly increased in the PPM-stimulated cells (PPM group) 30 minutes after stimulation. Meanwhile, compared to the PPM group, an increase in the GIP secretion rate was statistically significantly suppressed in the PPM-stimulated cells to which the FABP4/5 inhibitors were added (PPM+inhibitor group). There was a tendency that an increase in the secretion of GIP was dose-dependently suppressed in the PPM stimulation +BMS309403 addition group (FIG. 3A).

Example 4 Screening of an Agent for Suppressing GIP Level Elevation Based on the Activity of FABP5

Agents for suppressing GIP level elevation were screened based on the activity of FABP5. The effects of test substances on the activity of FABP5 were investigated by measuring the activity of FABP5 by utilizing antagonistic binding of test substances to the FABP5 protein. The principle of a method for measuring the activity of FABP5 used in the present Example is shown in FIG. 4. 1-anilinonaphthalene-8-sulfonic acid (1,8-ANS) is reported to be a substance which emits fluorescence upon binding to FABP5 (Hum. Mol. Genet., 2014, 23 (24): 6495 to 6511). 1,8-ANS is a substance which emits fluorescence only in hydrophobic environments, but not in hydrophilic environments (FIG. 4A). Meanwhile, in the presence of FABP5, binding of 1,8-ANS to FABP5 makes the surrounding environment hydrophobic, leading to the emission of fluorescence (FIG. 4B). However, when a substance having a smaller binding constant for FABP5 is present, such a substance will bind to FABP5 more preferentially than 1,8-ANS will, thereby preventing 1,8-ANS from emitting fluorescence (FIG. 4C). A test substance which is found to suppress an increase in the fluorescence intensity by the aforementioned method is a substance which binds to the FABP5 protein to inhibit the activity of FABP5.

(Measurement of the FABP5-Inhibiting Activities of Test Substances)

*Escherichia coli*-derived recombinant FABP5 was expressed by a routine procedure and purified. In 96-well plates, purified FABP5 protein, 1,8-ANS, and test substances were added and the plates were allowed to stand at room temperature for five minutes, followed by measurement of the fluorescence intensity with a plate reader (excitation wavelength: 355 nm, fluorescent wavelength: 480 nm). As the test substances, the FABP5 inhibitor having a suppressing action on GIP level elevation used in Example 3 (Compound 2) and fish oil, which is an oil having an suppressing action on GIP level elevation as will be demonstrated in a Reference Example 1 later, were used. The final concentration of test substances in this evaluation system was from 0.002% to 0.1% (w/v).

(Results)

The results of evaluation are shown in FIG. 5. Compared to buffer alone, FABP5 alone, or 1,8-ANS alone, a significant increase in the fluorescence intensity was observed when both FABP5 and 1,8-ANS were present. This increase in the fluorescence intensity was statistically significantly suppressed by the addition of the FABP5 inhibitor having a suppressing action on GIP level elevation (t-test, $p<0.05$). Further, the fluorescence intensity was also statistically significantly reduced (t-test, $p<0.05$) when fish oil, which is an oil having a suppressing action on GIP level elevation, was added. Meanwhile, the fluorescence intensity was not reduced when a test substance having no suppressing action on GIP level elevation was added (data not shown). These results show that the suppressing action of a test substance on GIP level elevation can be evaluated using the activity of FABP5 as an index.

Reference Example 1 Suppressing Action of Fish Oil on GIP Level Elevation

The suppressing action of fish oil on GIP level elevation was examined by a single diet test in mice. Mice (C57BL/6J, male, 8 weeks old, n=10, CLEA Japan, Inc.) were fasted for 18 hours and then allowed to eat powder feed, which was a high-fat (HF) diet (25% rapeseed oil+5% palm oil) or a fish oil diet (15.4% rapeseed oil+5% palm oil+9.6% fish oil (10% DHA)), ad libitum for 60 minutes. Blood was collected from the orbital sinus of each mouse before and 60, 120, and 240 minutes after ad libitum intake. The blood thus collected was centrifuged at 11,000 rpm, 4° C. for 10 minutes to prepare the plasma. The blood GIP concentration was measured with a GIP ELISA kit (for rat/mouse) (Merck Millipore Corporation). The changes over time in the amount of changes in the blood GIP concentration ($\Delta$GIP) in mice after intake of test diets and the iAUC (0-4 h) of the blood GIP concentration are shown in FIGS. 6A and 6B. Compared to the HF diet group, an increase in the blood GIP concentration was statistically significantly reduced in the fish oil diet group.

What is claimed is:

1. A method for evaluating or selecting an agent for suppressing GIP level elevation, comprising the following steps (A) to (D):
   (A) contacting a test substance with a mammal-derived tissue or cell capable of expressing an FABP5 gene, or an FABP5 protein;
   (B) measuring the expression level of the FABP5 gene, the expression level of the FABP5 protein, or the activity of the FABP5 protein in the mammal-derived tissue or cell;
   (C) comparing the expression level or activity measured in (B) with the expression level of an FABP5 gene, the expression level of an FABP5 protein, or the activity of an FABP5 protein in a control group; and
   (D) evaluating or selecting a test substance that reduces the expression level of the FABP5 gene, the expression level of the FABP5 protein, or the activity of the FABP5 protein as an agent for suppressing GIP level elevation based on results of (C).

2. The method according to claim 1, wherein, when the expression level or activity measured in (B) is statistically significantly reduced compared to the expression level or activity in the control group, the test substance is evaluated as having a suppressing effect on GIP level elevation.

3. The method according to claim 1, wherein, when the expression level or activity measured in (B) is 90% or less taking the expression level or activity in the control group as 100%, the test substance is evaluated as having a suppressing effect on GIP level elevation or an appetite suppressing effect.

4. The method of claim 1, wherein said method further comprises step (E) evaluating the ability of the test substance selected in (D) to suppress elevation of the GIP level.

5. A method for evaluating or selecting an agent for preventing and/or ameliorating obesity, comprising the following steps (A) to (D):
   (A) contacting a test substance with a mammal-derived tissue or cell capable of expressing an FABP5 gene, or an FABP5 protein;
   (B) measuring the expression level of the FABP5 gene, the expression level of the FABP5 protein, or the activity of the FABP5 protein in the mammal-derived tissue or cell;
   (C) comparing the expression level or activity measured in (B) with the expression level of an FABP5 gene, the expression level of an FABP5 protein, or the activity of an FABP5 protein in a control group; and
   (D) evaluating or selecting a test substance that reduces the expression level of the FABP5 gene, the expression level of the FABP5 protein, or the activity of the FABP5 protein as an agent preventing and/or ameliorating obesity based on results of (C).

6. The method according to claim 5, wherein, when the expression level or activity measured in (B) is statistically significantly reduced compared to the expression level or activity in the control group, the test substance is evaluated as having an obesity preventing and/or ameliorating effect.

7. The method according to claim 5, wherein, when the expression level or activity measured in (B) is 90% or less taking the expression level or activity in the control group as 100%, the test substance is evaluated as having an inhibitory effect on body weight gain.

8. A method for evaluating or selecting a body weight gain suppressant, comprising the following steps (A) to (D):
(A) contacting a test substance with a mammal-derived tissue or cell capable of expressing an FABP5 gene, or an FABP5 protein;
(B) measuring the expression level of the FABP5 gene, the expression level of the FABP5 protein, or the activity of the FABP5 protein in the mammal-derived tissue or cell;
(C) comparing the expression level or activity measured in (B) with the expression level of an FABP5 gene, the expression level of an FABP5 protein, or the activity of an FABP5 protein in a control group; and
(D) evaluating or selecting a test substance that reduces the expression level of the FABP5 gene, the expression level of the FABP5 protein, or the activity of the FABP5 protein as a body weight gain suppressant based on results of (C).

9. The method according to claim 8, wherein, when the expression level or activity measured in (B) is statistically significantly reduced compared to the expression level or activity in the control group, the test substance is evaluated as having an obesity preventing and/or ameliorating effect.

10. The method according to claim 8, wherein, when the expression level or activity measured in (B) is 90% or less taking the expression level or activity in the control group as 100%, the test substance is evaluated as having an inhibitory effect on body weight gain.

11. A method for detecting the presence of a GIP elevation inhibitor in a test substance, comprising the following steps (A)-(B):
(A) contacting a test substance with a mammal-derived tissue or cell capable of expressing an FABP5 gene or an FABP5 protein; and
(B) detecting the presence of the GIP elevation inhibitor in the test substance by measuring a reduction in the expression level of the FABP5 gene, a reduction in the expression level of the FABP5 protein, or a reduction in the activity of the FABP5 protein in the mammal-derived tissue or cell as a result of the contacting in step (A).

* * * * *